(12) United States Patent
Kagermeier

(10) Patent No.: US 8,457,713 B2
(45) Date of Patent: Jun. 4, 2013

(54) MEDICAL TREATMENT SYSTEM

(75) Inventor: Robert Kagermeier, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 769 days.

(21) Appl. No.: 11/903,365

(22) Filed: Sep. 21, 2007

(65) Prior Publication Data

US 2008/0081992 A1 Apr. 3, 2008

(30) Foreign Application Priority Data

Sep. 29, 2006 (DE) .......................... 10 2006 046 689

(51) Int. Cl.
*A61B 5/05* (2006.01)

(52) U.S. Cl.
USPC ........... 600/411; 600/407; 600/437; 600/410; 378/63; 378/87; 378/90

(58) Field of Classification Search
USPC .............. 700/258, 245; 5/510, 86.1; 600/407, 600/409
See application file for complete search history.

(56) References Cited

U.S. PATENT DOCUMENTS

| | | | |
|---|---|---|---|
| 5,603,328 A * | 2/1997 | Zucker et al. ................. | 600/479 |
| 5,835,558 A | 11/1998 | Maschke | |
| 6,263,231 B1 | 7/2001 | Reitter | |
| 6,431,751 B1 * | 8/2002 | Everett et al. ................. | 378/197 |
| 2003/0093503 A1 * | 5/2003 | Yamaki et al. ................ | 709/220 |
| 2003/0182019 A1 * | 9/2003 | Bonini et al. ................. | 700/242 |
| 2004/0093650 A1 * | 5/2004 | Martins et al. ..................... | 901/1 |
| 2004/0179332 A1 * | 9/2004 | Smith et al. .................... | 361/681 |
| 2005/0209614 A1 * | 9/2005 | Fenter et al. ................... | 606/153 |
| 2007/0045019 A1 * | 3/2007 | Carter et al. ................... | 180/167 |

FOREIGN PATENT DOCUMENTS

| | | |
|---|---|---|
| DE | 43 17 716 A1 | 3/1994 |
| DE | 295 10 803 U1 | 11/1995 |
| DE | 196 27 657 A1 | 1/1998 |
| DE | 198 49 764 A1 | 5/2000 |

OTHER PUBLICATIONS

German Office Action dated Jul. 18, 2007 for DE 10 2006 046 689.6-35 with English translation.

* cited by examiner

*Primary Examiner* — Tse Chen
*Assistant Examiner* — Joel F Brutus
(74) *Attorney, Agent, or Firm* — Lempia Summerfield Katz LLC

(57) ABSTRACT

A medical treatment system is provided. The medical treatment system includes a medical imaging unit and a mobile display device mechanically disconnected from the medical imaging unit, a control unit, an input device. A data transmission device is operable to transmit data recorded by the medical imaging unit to the mobile display device. A vehicle supports the mobile display device and includes a drive unit. The control unit, operating in conjunction with the input device, is operable to control the display device and the drive unit.

20 Claims, 1 Drawing Sheet

MEDICAL TREATMENT SYSTEM

This application claims the benefit of DE 10 2006 046 689.6, filed Sep. 29, 2006, which is hereby incorporated by reference.

BACKGROUND

The present embodiments relate to a medical treatment system. The term "treatment system" refers to examination systems, diagnostic systems, and therapy systems.

DE 198 49 764 B4 discloses a diagnostic imaging apparatus designed to acquire image information representing at least one area of an object under examination and incorporating a signal processing apparatus. The diagnostic imaging apparatus may include an x-ray source and a radiation receiver mounted at the ends of a C-arm, which is adjustable along its circumference. The C-arm is pivotable about its central axis, so that a central ray of a radiation beam emitted by the x-ray radiator intersects the central axis at right angles. The image information acquired by the C-arm unit is fed, after processing by an image processing apparatus, to a monitor displaying the corresponding images. DE 198 49 764 B4 makes no mention of the disposition of the monitor.

DE 196 27 657 C2 discloses a diagnostic imaging apparatus, such as an x-ray unit. DE 196 27 657 C2 discloses a mobile x-ray unit including a trolley on top of which are mounted two jointed arms that support respectively an x-ray source and a flat panel detector, which can both be adjusted three-dimensionally. The flat panel detector is a matrix of detector elements and connected to imaging electronics disposed in the trolley. The image signals supplied by the imaging electronics are fed to a monitor via a plug connection. The monitor that reproduces the x-ray images may be mounted directly on the trolley. Accordingly, DE 196 27 657 C2 discloses a diagnostic apparatus that has all the components required for taking x-rays and allows immediate viewing of the x-ray images.

Two people are generally required to operate a diagnostic apparatus such as a C-arm unit. In the case of a mobile C-arm x-ray system, for example, for displaying the x-ray image information at least one monitor can be mounted on a wheeled monitor trolley, the actual C-arm x-ray unit and the monitor trolley being maneuverable separately. The monitor trolley has to be manually positioned and adjusted depending on the settings of the C-arm x-ray unit. Transportation of the entire x-ray system necessitates the simultaneous deployment of a plurality of people or time-consuming sequential handling by a single operator.

SUMMARY

The present embodiments may obviate one or more of the limitations or drawbacks inherent in the related art. For example, one embodiment simplifies the operation of an imaging-type medical treatment system, such as an x-ray system.

In one embodiment, a treatment system includes a medical imaging unit, a mobile display device not mechanically connected to the medical imaging unit, a control unit, and an input device that supplies input data to the control unit. Data recorded using the imaging unit is transmitted to the mobile display device by, for example, a radio-based data transmission device. The mobile display device is mechanically connected to a wheeled stand having an autonomous drive unit. The drive unit and display device are controlled via the input device operating in conjunction with the control unit. The wheeled stand, which supports the display device and can be moved separately from the imaging unit, is incorporated into the control of the treatment system as a whole, such as the motor drive. A single person may efficiently operate the complete medical treatment system, such as an x-ray treatment system. The imaging unit provided as a component of the treatment system is a mobile C-arm x-ray unit, a computed tomography unit, magnetic resonance unit, or angiography unit. Alternatively, the imaging unit is a therapy unit, such as a radiation therapy unit or a lithotripsy unit.

The input device may be based on any physical principle of signal acquisition or on a combination of different signal acquisition methods. Possible methods include, for example, optical acquisition systems, acoustic acquisition systems, and contactless distance detection systems. An input may be provided either by an operator or automatically. The input device may be implemented as part of the imaging unit, as part of the wheeled stand supporting the display device, also known as the monitor trolley, or as a separate operator control or data acquisition unit.

An optical signal acquisition system may include a camera system, which provides two-dimensional (2D) or three-dimensional (3D) image information in real-time. In a 3D image acquisition system, a 3D time-of-flight solid state sensor system allows object detection including gesture recognition. The sensor system suitable for object detection may include a transmitting device, for example, an infrared or radar transmitter, operating in conjunction with a time measuring device and a corresponding detection device. Three-dimensional information, requiring minimal data processing capacities, may be provided using the the sensor system.

In one embodiment, an input device employs an acoustic signal acquisition. The monitor trolley may be controlled by a voice. At least one sensor, for example, a microphone, operating in conjunction with the control unit may be disposed on the monitor trolley or on any other component of the medical treatment system. The display device may be hinged to the wheeled stand in a preferably power-adjustable manner. Accordingly, the position of the wheeled stand as a whole and the positioning of the monitor on the wheeled stand are adjustable by voice control.

In one embodiment, the input device incorporates distance sensors. The sensors may be linked into the control system, which allows automatic maneuvering of the monitor trolley as a function of the positioning and/or setting of the imaging diagnostic unit. The position of the monitor trolley relative to the diagnostic unit and/or the absolute position of the monitor trolley and diagnostic unit may be continuously determined by a navigation system. A collision warning system, which displays to the operator an impending collision of various adjustable components of the treatment system and/or automatically prevents such a collision, may be incorporated into a navigation system. A satellite-based navigation system, for example, for automatic navigation using stored card material, is expediently employed, as is used, for example, for navigation in road traffic.

The drive unit of the monitor trolley may be electrically operated using a suitably dimensioned energy storage device, for example, a lead-gel battery, disposed in the wheeled stand. A fixed charging station may charge up the energy store, i.e., for indirectly supplying power to the wheeled stand. In one embodiment, the charging station may be linked into the sensor-based navigation system, the monitor trolley automatically moving to the charging station and automatically hooking up to the charging station on completion of an examination carried out using the treatment system.

In one embodiment, the wheeled stand, which supports at least one monitor, includes one, two, or more remotely controllable jointed arms. The monitor trolley may be used for viewing images assuming the functionality of a remote-controlled, such as a voice-controlled, assistance system that supports the doctor as an operator during an intervention. The manpower requirement may be reduced by dispensing with the operator of the treatment system. The wholly or partly automatic monitor trolley maneuvering function may be deactivated if the trolley assumes more advanced functions as a jointed arm robot. The more advanced functions of the monitor trolley turn the monitor trolley into a monitor/assistance trolley that has a wide variety of uses in conjunction with different diagnostic/therapy systems.

In one embodiment, a monitor trolley tracked in a remotely controlled or fully automatic manner allows particularly easy, efficient operation of an imaging diagnostic unit having collectively movable or at least adjustable parts.

DETAILED DESCRIPTION

Figure 1:
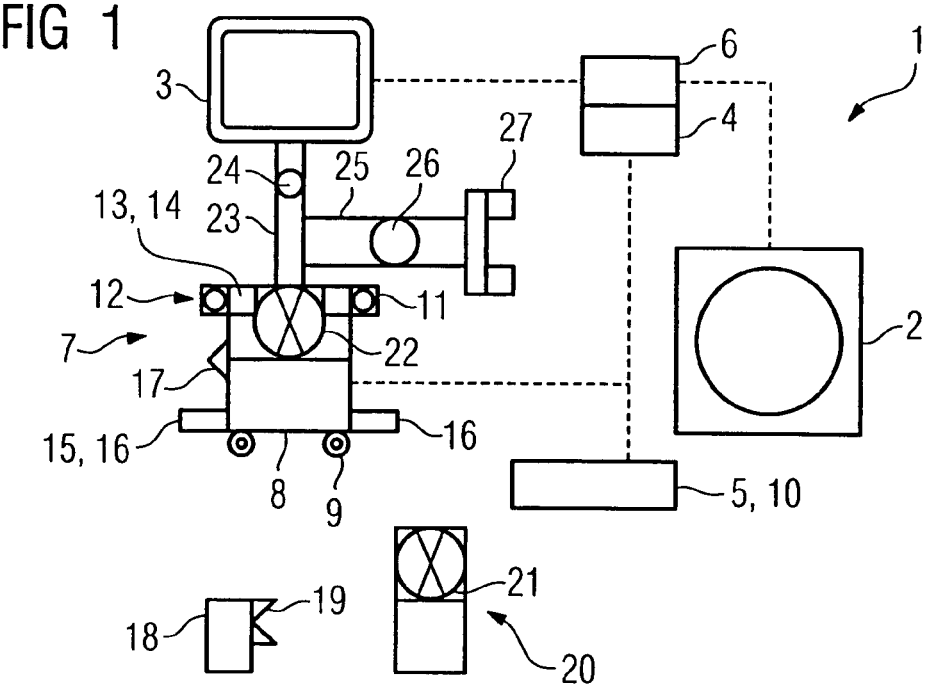
FIG. 1 schematically illustrates one embodiment of a medical treatment system.
Figure 2:
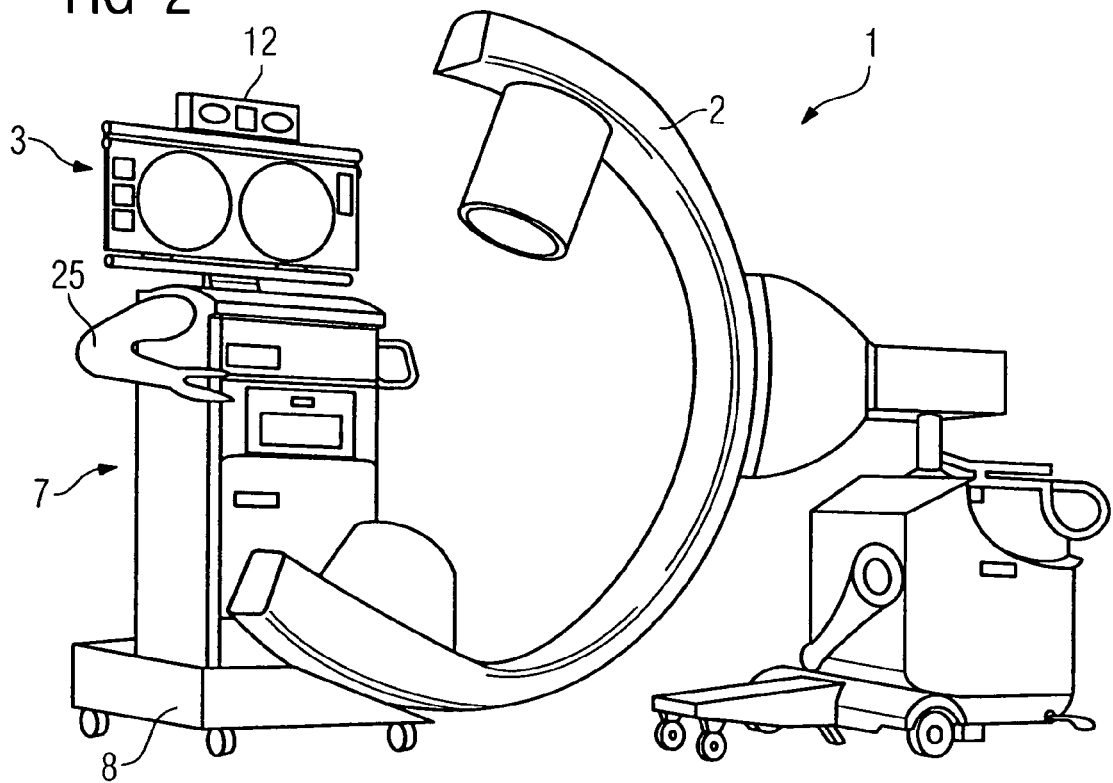
FIG. 2 shows a three-dimensional view of the medical treatment system according to FIG. 1.

In one embodiment, as shown in FIGS. 1 and 2, a medical treatment system 1 includes an imaging diagnostic unit 2, such as a C-arm x-ray unit, and a mobile display device 3. The mobile display device 3 displays x-ray images obtained by the diagnostic unit 2. The imaging diagnostic device 2 may also be, for example, a computed tomography unit.

The medical treatment system 1 may include a control unit 4. The control unit 4 is a data interface between the diagnostic unit 2 and the display device 3, i.e. the monitor provided for displaying x-ray images captured by the diagnostic device 2. As an alternative to the schematic representation in FIG. 1, a control unit 4 may be incorporated into the imaging diagnostic unit 2 or another component of the treatment system 1. An input or operating device 5 acting in conjunction with the control unit 4 may be incorporated into the imaging diagnostic unit 2 or another component of the treatment system 1. A data transmission device 6, which is designed to establish a wireless connection, such as a radio link, between the imaging diagnostic unit 2 and the display device 3 may be incorporated into the imaging diagnostic unit 2 or another component of the treatment system 1.

The monitor 3 is mounted on a vehicle (cart) 7 also termed a monitor trolley, which has a drive unit 8 for automatic maneuvering. The drive unit 8 may be an electromotive drive. Individual wheels 9 of the vehicle 7 may be steerable and/or driven, for example, with the drive unit 8. The vehicle 7, which includes the display device 3 and the drive unit 8, is not mechanically connected in any way to the imaging diagnostic unit 2. For example, there is no cable connection between the vehicle 7 and the diagnostic unit 2. The x-ray image information generated by the diagnostic unit 2 is displayed on the monitor 3 in real-time, i.e. without perceptible delay, and in sufficient image quality even for interventional purposes.

In one embodiment, as shown in FIG. 2, the imaging diagnostic unit 2 is maneuverable. Individual components of the C-arm unit used as the diagnostic unit 2, as known in principle, e.g. from DE 198 49 764 B4 mentioned in the introduction, are likewise adjustable. The optimum position of the vehicle 7, also known as a monitor trolley, varies depending on the selected position and the settings of the diagnostic unit 2.

In one embodiment, the vehicle 7 is maneuverable. The vehicle 7 can be controlled by the drive unit 8. The drive unit 8 may be remotely controlled by the operator of the medical treatment system 1 by input, e.g. a keyboard, joystick or mouse input, by the input device 5, implemented by way of example as a keyboard 10. Semiautomatic or completely automatic maneuvering of the vehicle 7 is also possible. The vehicle 7 may be equipped with a plurality of different input devices 5, for example, an optical acquisition system 12 incorporating two cameras 11, an acoustic acquisition system 14 employing at least one microphone 13, and a distance detection system 16 having a number of sensors 15. The sensors 15 may be, for example, laser scanners, infrared sensors, or ultrasound sensors.

The different acquisition systems 12 of the monitor trolley 7 operating as input devices 5 can be used in various ways for remotely controlled, semiautomatic, or fully automatic navigation of the vehicle (wheeled stand) 7. The optical acquisition system 12 may detect gestures of the operator of the treatment system 1. For example, the optical acquisition system 12 assumes functions which can be performed by the keyboard 10. The optical acquisition system 12 may detect the geometrical position of units located in the room, such as the positioning of subcomponents of the diagnostic unit 2, and use this information to control the drive unit 8.

In one embodiment, the acoustic acquisition system 14 is exclusively processes voice commands entered by the user. A microphone, which can be worn by the user, for example, in the form of a headset, wirelessly transmits the voice commands. The diagnostic unit 2, or some other apparatus, may include (e.g, on or in) a microphone, for example, a directional microphone and/or a microphone with speaker locating function. As with the optical acquisition system 12, prioritizing rules can specify, for example, that the control unit 4 always executes a command entered via the keyboard 10 even if a voice or gesture input contradicting that command is simultaneously detected. The control unit 4 may be set, for example, by software in such a way that, in the event of contradictory inputs, none of the corresponding actions are executed, but a relevant message is output, for example, by the monitor 3.

In one embodiment, the distance detection system 16, in contrast to the optical acquisition system 12 and the acoustic acquisition system 14 (which detect commands deliberately entered by the operator), detect automatic control and safety functions. The distance detection system 16 may be linked to the optical acquisition system 12. Accordingly, there may be redundancy with respect to the safety functions in areas covered by the two acquisition systems 14, 16.

In one embodiment, the vehicle 7 is a computer-based support vehicle. The vehicle 7 may be battery-operated and include a charging terminal 17, which allows charging without opening the vehicle 7. A fixed charging station 18 may be used to charge the battery operated drive unit 8. The fixed charging station 18 has a charging terminal 19 compatible with the charging terminal 17.

In one embodiment, the vehicle 7 may be automatically moved toward the charging station 18. For this purpose, a navigation system 20 may operate, for example, on a radio or infrared basis and at a variance with the illustration in FIG. 1, can be incorporated, for example, into the data transmission device 6. The navigation system 20 may include a fixed central navigation unit 21, such as a transceiver. A navigation unit 22 may be built into the vehicle 7 or permanently connected to same. Conversely, the navigation system 20 may include the acquisition systems 12, 14, 16.

The control unit 4, which may be operated by the input device 5, enables the drive unit 8 to be controlled and allows powered adjustment of the monitor 3 on the vehicle 7. For this purpose, the monitor 3 may be attached to a swivel neck 23 hinged to the vehicle 7 and having at least one joint 24. Both the vehicle 7 and the swivel neck 23 may be operated under remote control by the operator or partially or fully automatically.

In one embodiment, as shown in FIG. 1, the vehicle 7 may support, in addition to the monitor 3, a jointed arm 25 having at least one joint 26. The jointed arm 25 and at least one joint 26 may be a robot arm. The jointed arm 25 may be hinged to the vehicle 7 independently of the swivel neck 23. A tool 27, for example, a gripper may be attached to the jointed arm 25. Accordingly, the automatically navigable vehicle; 7 can be used as an assistance system for diagnostic and/or therapeutic interventions.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical system comprising:
   a medical imaging unit,
   a mobile display device mechanically disconnected from the medical imaging unit,
   a control unit,
   an input device,
   a data transmission device that is operable to transmit data recorded by the medical imaging unit to the mobile display device, and
   a vehicle that supports the mobile display device and includes a drive unit and a collision warning system, the drive unit configured to move the vehicle relative to the medical imaging unit, and the collision warning system configured to detect an impending collision of two or more components of the medical system and to display, via the mobile display device, an indication of the impending collision,
   wherein the control unit, operating in conjunction with the input device, is configured to control the mobile display device and the drive unit, and
   wherein the input device includes an optical acquisition system configured to detect gesture commands from an operator of the medical system or an acoustic acquisition system configured to detect voice commands from the operator of the medical system, the control unit being configured to automatically control a position of the vehicle via the drive unit based on the detected gesture commands or the detected voice commands.

2. The medical system as claimed in claim 1, wherein the medical imaging unit is a diagnostic unit.

3. The medical system as claimed in claim 2, wherein the diagnostic unit includes a C-arm x-ray unit, a computed tomography unit, a magnetic resonance unit, or an angiography unit.

4. The medical system as claimed in claim 1, wherein the medical imaging unit includes a therapy unit.

5. The medical system as claimed in claim 4, wherein the therapy unit includes a radiation therapy unit or a lithotripsy unit.

6. The medical system as claimed in claim 1, wherein the input device includes a distance detection system.

7. The medical system as claimed in claim 1, wherein the display device is hinged to the vehicle in a power-adjustable manner.

8. The medical system as claimed in claim 1, comprising a fixed charging station that is operable to supply power to the vehicle.

9. The medical system as claimed in claim 8, wherein the vehicle includes a rechargeable-battery.

10. The medical system as claimed in claim 1, comprising a navigation system that is operable to automatically maneuver the vehicle.

11. The medical system as claimed in claim 1, wherein the vehicle includes a remotely controllable jointed arm.

12. The medical system as claimed in claim 1, wherein the vehicle is a wheeled stand.

13. The medical system as claimed in claim 1, wherein the vehicle is a cart.

14. The medical system as claimed in claim 1, wherein the optical acquisition system is configured to detect settings or a position of the medical imaging unit, and wherein the control unit, operating in conjunction with the input device, is configured to automatically control the drive unit to position the vehicle based on the detected settings or position of the medical imaging unit.

15. The medical system as claimed in claim 1, wherein the control unit, operating in conjunction with the input device, is operable to wirelessly control the mobile display device and the drive unit.

16. The medical system as claimed in claim 1, wherein the vehicle comprises a plurality of wheels, and wherein the drive unit is operable to drive the plurality of wheels to move the vehicle along a floor surface supporting the vehicle.

17. The medical system as claimed in claim 1, wherein the control unit is further configured to control a position of at least part of the mobile display device relative to the vehicle based on the detected gesture commands or the detected voice commands.

18. The medical system as claimed in claim 1, wherein the input device includes the optical acquisition system and the acoustic acquisition system, and wherein the control unit is configured to control the position of the vehicle via the drive unit and control a position of at least part of the mobile display device relative to the vehicle based on the detected gesture commands, the detected voice commands, or a combination thereof.

19. A medical system comprising:
   a medical imaging unit,
   a mobile display device mechanically disconnected from the medical imaging unit,
   a control unit,
   an input device,
   a data transmission device that is operable to transmit data recorded by the medical imaging unit to the mobile display device, and
   a vehicle that supports the mobile display device and includes a remotely controllable jointed arm, a drive unit configured to control a position of the vehicle relative to the medical imaging unit, and a collision warning system configured to detect an impending collision of two or more components of the medical system and to display, via the mobile display device, an indication of the impending collision,
   wherein the control unit, operating in conjunction with the input device, is configured to control the mobile display device and the drive unit,
   wherein the input device includes (i) an optical acquisition system configured to detect gesture commands from an operator of the medical system or settings or a position of the medical imaging unit, (ii) an acoustic acquisition system configured to detect voice commands from the operator of the medical system, and (iii) a distance detection system having a plurality of sensors, the control unit being configured to adjust the position of the vehicle via the drive unit or control a position of at least part of the mobile display device relative to the vehicle based on the detected settings or position of the medical imaging unit, the detected gesture commands, the detected voice commands, or combinations thereof, and
   wherein the remotely controllable jointed arm is configured to be controlled based on the detected voice commands.

20. A medical system comprising:
   a medical imaging unit,
   a mobile display device mechanically disconnected from the medical imaging unit, a control unit,
an input device,
a data transmission device that is operable to transmit data recorded by the medical imaging unit to the mobile display device, and
a vehicle that supports the mobile display device and includes a drive unit configured to move the vehicle and a collision warning system configured to detect an impending collision of two or more components of the medical system and to display, via the mobile display device, an indication of the impending collision,
wherein the control unit, operating in conjunction with the input device, is configured to control the mobile display device and the drive unit, and
wherein the input device includes an optical acquisition system configured to detect gesture commands from an operator of the medical system, the control unit being configured to adjust the position of the vehicle via the drive unit, control a position of at least part of the mobile display device relative to the vehicle, or a combination thereof, based on the detected gesture commands.

\* \* \* \* \*